US010585207B2

(12) United States Patent
Morton

(10) Patent No.: US 10,585,207 B2
(45) Date of Patent: Mar. 10, 2020

(54) SCANNING SYSTEMS

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 278 days.

(21) Appl. No.: 14/948,788

(22) Filed: Nov. 23, 2015

(65) Prior Publication Data

US 2016/0274267 A1 Sep. 22, 2016

Related U.S. Application Data

(63) Continuation of application No. 12/919,484, filed as application No. PCT/GB2009/000575 on Feb. 27, 2009, now Pat. No. 9,223,052.

(30) Foreign Application Priority Data

Feb. 28, 2008 (GB) .................................. 0803644.4

(51) Int. Cl.
 *G01V 5/00* (2006.01)
(52) U.S. Cl.
 CPC .......... *G01V 5/0083* (2013.01); *G01V 5/0066* (2013.01); *G01N 2223/639* (2013.01); *G05B 2219/42222* (2013.01)
(58) Field of Classification Search
 CPC .. G01V 5/0083; G01V 5/0008; G01V 5/0066; G05B 2219/42222; G01N 2223/639
 See application file for complete search history.

(56) References Cited

U.S. PATENT DOCUMENTS

| | | |
|---|---|---|
| 2,952,790 A | 9/1960 | Steen |
| 3,146,349 A | 8/1964 | Jordan |
| 3,239,706 A | 3/1966 | Farrell |
| 3,458,026 A | 7/1969 | Lauzon |
| 3,485,339 A | 12/1969 | Miller |
| 3,768,645 A | 10/1973 | Conway |
| 3,955,678 A | 5/1976 | Moyer |
| 3,980,889 A | 9/1976 | Haas |
| 4,057,725 A | 11/1977 | Wagner |

(Continued)

FOREIGN PATENT DOCUMENTS

| | | |
|---|---|---|
| CN | 101303317 A | 11/2008 |
| DE | 2729353 A1 | 1/1979 |

(Continued)

OTHER PUBLICATIONS

US 5,987,079 A, 11/1999, Scott (withdrawn)

(Continued)

*Primary Examiner* — Christopher E. Everett
(74) *Attorney, Agent, or Firm* — Novel IP

(57) ABSTRACT

The present application is directed toward cargo scanning systems having scanners, each arranged to scan a respective object and generate a set of scan data, processors arranged to process each set of scan data to determine whether it meets a predetermined threat condition, workstations, and data management system arranged to direct data that meets the threat condition to one of the workstations for analysis.

17 Claims, 3 Drawing Sheets

(56) References Cited

U.S. PATENT DOCUMENTS

| | | |
|---|---|---|
| 4,105,922 A | 8/1978 | Lambert |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,340,816 A | 7/1982 | Schott |
| 4,352,021 A | 9/1982 | Boyd |
| 4,366,382 A | 12/1982 | Kotowski |
| 4,468,802 A | 8/1984 | Friedel |
| 4,626,688 A | 12/1986 | Barnes |
| 4,672,649 A | 6/1987 | Rutt |
| 4,675,890 A | 6/1987 | Plessis |
| 4,709,382 A | 11/1987 | Sones |
| 4,817,123 A | 3/1989 | Sones |
| RE32,961 E | 6/1989 | Wagner |
| 4,866,439 A | 9/1989 | Kraus |
| 4,866,745 A | 9/1989 | Akai |
| 4,868,856 A | 9/1989 | Frith |
| 4,872,188 A | 10/1989 | Lauro |
| 4,887,604 A | 12/1989 | Shefer |
| 4,979,137 A | 12/1990 | Gerstenfeld |
| 4,987,584 A | 1/1991 | Doenges |
| 4,991,708 A | 2/1991 | Francioni |
| 5,033,106 A | 7/1991 | Kita |
| 5,086,300 A | 2/1992 | Ash more |
| 5,092,451 A | 3/1992 | Jones |
| 5,097,939 A | 3/1992 | Shanklin |
| 5,144,191 A | 9/1992 | Jones |
| 5,182,764 A | 1/1993 | Peschmann |
| 5,221,843 A | 6/1993 | Alvarez |
| 5,243,693 A | 9/1993 | Maron |
| 5,247,556 A | 9/1993 | Eckert |
| 5,247,561 A | 9/1993 | Kotowski |
| 5,259,014 A | 11/1993 | Brettschneider |
| 5,272,627 A | 12/1993 | Maschhoff |
| 5,313,511 A | 5/1994 | Annis |
| 5,319,547 A | 6/1994 | Krug |
| 5,341,916 A | 8/1994 | Doane |
| 5,367,552 A | 11/1994 | Peschmann |
| 5,410,156 A | 4/1995 | Miller |
| 5,412,702 A | 5/1995 | Sata |
| 5,467,377 A | 11/1995 | Dawson |
| 5,490,196 A | 2/1996 | Rudich |
| 5,490,218 A | 2/1996 | Krug |
| 5,505,291 A | 4/1996 | Huang |
| 5,511,104 A | 4/1996 | Mueller |
| 5,548,123 A | 8/1996 | Perez-Mendez |
| 5,557,108 A | 9/1996 | Tumer |
| 5,590,057 A | 12/1996 | Fletcher |
| 5,600,303 A | 2/1997 | Husseiny |
| 5,600,700 A | 2/1997 | Krug |
| 5,604,778 A | 2/1997 | Polacin |
| 5,606,167 A | 2/1997 | Miller |
| 5,633,907 A | 5/1997 | Gravelle |
| 5,634,551 A | 6/1997 | Francioni |
| 5,642,393 A * | 6/1997 | Krug .................... G01V 5/0016 376/159 |
| 5,660,549 A | 8/1997 | Witt |
| 5,661,774 A | 8/1997 | Gordon |
| 5,689,541 A | 11/1997 | Schardt |
| 5,712,926 A | 1/1998 | Eberhard |
| 5,738,202 A | 4/1998 | Ydoate |
| 5,764,683 A | 6/1998 | Swift |
| 5,796,802 A | 8/1998 | Gordon |
| 5,818,897 A | 10/1998 | Gordon |
| 5,838,758 A | 11/1998 | Krug |
| 5,841,831 A | 11/1998 | Hell |
| 5,859,891 A | 1/1999 | Hibbard |
| 5,870,449 A | 2/1999 | Lee |
| 5,881,122 A | 3/1999 | Crawford |
| 5,882,206 A | 3/1999 | Gillio |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,910,973 A | 6/1999 | Grodzins |
| 5,930,326 A | 7/1999 | Rothschild |
| 5,949,842 A | 9/1999 | Schafer |
| 5,963,211 A | 10/1999 | Oikawa |
| 5,966,422 A | 10/1999 | Dafni |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,143 A | 2/2000 | Simanovsky |
| 6,026,171 A | 2/2000 | Hiraoglu |
| 6,035,014 A | 3/2000 | Hiraoglu |
| 6,037,597 A | 3/2000 | Karavolos |
| 6,044,353 A | 3/2000 | Pugliese |
| 6,067,366 A | 5/2000 | Simanovsky |
| 6,073,751 A | 6/2000 | Worzischek |
| 6,075,871 A | 6/2000 | Simanovsky |
| 6,076,400 A | 6/2000 | Bechwati |
| 6,078,642 A | 6/2000 | Simanovsky |
| 6,088,423 A | 7/2000 | Krug |
| 6,091,795 A | 7/2000 | Schafer |
| 6,108,396 A | 8/2000 | Bechwati |
| 6,111,974 A | 8/2000 | Hiraoglu |
| 6,118,852 A | 9/2000 | Rogers |
| 6,122,343 A | 9/2000 | Pidcock |
| 6,128,365 A | 10/2000 | Bechwati |
| 6,137,895 A | 10/2000 | Al-Sheikh |
| 6,149,592 A | 11/2000 | Yanof |
| 6,163,591 A | 12/2000 | Benjamin |
| 6,181,765 B1 | 1/2001 | Sribar |
| 6,183,139 B1 | 2/2001 | Solomon |
| 6,185,272 B1 | 2/2001 | Hiraoglu |
| 6,188,745 B1 | 2/2001 | Gordon |
| 6,195,444 B1 | 2/2001 | Simanovsky |
| 6,216,540 B1 | 4/2001 | Nelson |
| 6,218,943 B1 * | 4/2001 | Ellenbogen .......... G01V 5/0008 340/572.1 |
| 6,236,709 B1 | 5/2001 | Perry |
| 6,246,320 B1 | 6/2001 | Monroe |
| 6,252,929 B1 | 6/2001 | Swift |
| 6,256,404 B1 | 7/2001 | Gordon |
| 6,269,142 B1 | 7/2001 | Smith |
| 6,272,230 B1 | 8/2001 | Hiraoglu |
| 6,292,533 B1 | 9/2001 | Swift |
| 6,301,327 B1 | 10/2001 | Martens |
| 6,304,629 B1 | 10/2001 | Conway |
| 6,317,509 B1 | 11/2001 | Simanovsky |
| 6,324,243 B1 | 11/2001 | Edic |
| 6,324,249 B1 | 11/2001 | Fazzio |
| 6,345,113 B1 | 2/2002 | Crawford |
| 6,370,222 B1 * | 4/2002 | Cornick, Jr. ......... G01V 5/0016 378/57 |
| 6,418,189 B1 | 7/2002 | Schafer |
| 6,429,578 B1 | 8/2002 | Danielsson |
| 6,430,255 B2 | 8/2002 | Fenkart |
| 6,431,344 B1 | 8/2002 | Emmermann |
| 6,445,765 B1 | 9/2002 | Frank |
| 6,446,782 B1 | 9/2002 | Patrick |
| 6,459,755 B1 | 10/2002 | Li |
| 6,459,761 B1 | 10/2002 | Grodzins |
| 6,459,764 B1 | 10/2002 | Chalmers |
| 6,507,025 B1 | 1/2003 | Verbinski |
| 6,542,580 B1 * | 4/2003 | Carver .................. G01N 23/04 378/57 |
| 6,546,072 B1 | 4/2003 | Chalmers |
| 6,549,683 B1 | 4/2003 | Bergeron |
| 6,552,346 B2 | 4/2003 | Verbinski |
| 6,556,653 B2 | 4/2003 | Hussein |
| 6,563,906 B2 | 5/2003 | Hussein |
| 6,590,956 B2 | 7/2003 | Fenkart |
| 6,618,466 B1 | 9/2003 | Ning |
| 6,629,593 B2 | 10/2003 | Zeitler |
| 6,647,091 B2 | 11/2003 | Fenkart |
| 6,647,094 B2 | 11/2003 | Harding |
| 6,647,095 B2 | 11/2003 | Hsieh |
| 6,687,333 B2 | 2/2004 | Carroll |
| 6,690,766 B2 | 2/2004 | Kresse |

(56) References Cited

U.S. PATENT DOCUMENTS

| | | | |
|---|---|---|---|
| 6,707,879 B2 * | 3/2004 | McClelland | B64F 1/368 378/57 |
| 6,715,533 B2 | 4/2004 | Kresse | |
| 6,721,387 B1 | 4/2004 | Naidu | |
| 6,721,391 B2 | 4/2004 | McClelland | |
| 6,735,271 B1 | 5/2004 | Rand | |
| 6,737,652 B2 | 5/2004 | Lanza | |
| 6,748,043 B1 | 6/2004 | Dobbs | |
| 6,754,298 B2 | 6/2004 | Fessler | |
| 6,760,407 B2 | 7/2004 | Price | |
| 6,770,884 B2 | 8/2004 | Bryman | |
| 6,775,348 B2 | 8/2004 | Hoffman | |
| 6,788,761 B2 | 9/2004 | Bijjani | |
| 6,812,426 B1 | 11/2004 | Kotowski | |
| 6,813,374 B1 | 11/2004 | Karimi | |
| 6,816,571 B2 | 11/2004 | Bijjani | |
| 6,827,265 B2 | 12/2004 | Knowles | |
| 6,829,585 B1 * | 12/2004 | Grewal | G06Q 10/02 379/265.05 |
| 6,830,185 B2 | 12/2004 | Tsikos | |
| 6,837,432 B2 | 1/2005 | Tsikos | |
| 6,856,667 B2 | 2/2005 | Ellenbogen | |
| 6,859,514 B2 | 2/2005 | Hoffman | |
| 6,899,540 B1 | 5/2005 | Neiderman | |
| 6,901,135 B2 | 5/2005 | Fox | |
| 6,901,346 B2 | 5/2005 | Tracy | |
| 6,906,329 B2 | 6/2005 | Bryman | |
| 6,907,101 B2 | 6/2005 | Hoffman | |
| 6,922,455 B2 | 7/2005 | Jurczyk | |
| 6,922,460 B2 | 7/2005 | Skatter | |
| 6,922,461 B2 | 7/2005 | Kang | |
| 6,928,141 B2 | 8/2005 | Carver | |
| 6,933,504 B2 | 8/2005 | Hoffman | |
| 6,934,354 B2 | 8/2005 | Hoffman | |
| 6,940,071 B2 | 9/2005 | Ramsden | |
| 6,944,264 B2 | 9/2005 | Bijjani | |
| 6,947,517 B2 | 9/2005 | Hoffman | |
| 6,950,492 B2 | 9/2005 | Besson | |
| 6,950,493 B2 | 9/2005 | Besson | |
| 6,952,163 B2 | 10/2005 | Huey | |
| 6,953,935 B1 | 10/2005 | Hoffman | |
| 6,957,913 B2 | 10/2005 | Renkart | |
| 6,962,289 B2 | 11/2005 | Vatan | |
| 6,968,030 B2 | 11/2005 | Hoffman | |
| 6,968,034 B2 | 11/2005 | Ellenbogen | |
| 6,971,577 B2 | 12/2005 | Tsikos | |
| 6,973,158 B2 | 12/2005 | Besson | |
| 6,975,698 B2 | 12/2005 | Katcha | |
| 6,978,936 B2 | 12/2005 | Tsikos | |
| 6,980,627 B2 | 12/2005 | Qiu | |
| 6,990,171 B2 | 1/2006 | Toth | |
| 6,990,172 B2 | 1/2006 | Toth | |
| 6,991,371 B2 | 1/2006 | Georgeson | |
| 6,993,115 B2 | 1/2006 | McGuire | |
| 6,996,209 B2 | 2/2006 | Marek | |
| 7,010,083 B2 | 3/2006 | Hoffman | |
| 7,016,459 B2 | 3/2006 | Ellenbogen | |
| 7,020,241 B2 | 3/2006 | Beneke | |
| 7,020,242 B2 | 3/2006 | Ellenbogen | |
| 7,023,956 B2 | 4/2006 | Heaton | |
| 7,023,957 B2 | 4/2006 | Bijjani | |
| 7,027,553 B2 | 4/2006 | Dunham | |
| 7,027,554 B2 | 4/2006 | Gaultier | |
| 7,031,430 B2 | 4/2006 | Kaucic | |
| 7,031,434 B1 | 4/2006 | Saunders | |
| 7,034,313 B2 | 4/2006 | Hoffman | |
| 7,039,154 B1 | 5/2006 | Ellenbogen | |
| 7,042,975 B2 | 5/2006 | Heuscher | |
| 7,045,787 B1 | 5/2006 | Verbinski | |
| 7,046,756 B2 | 5/2006 | Hoffman | |
| 7,046,761 B2 | 5/2006 | Ellenbogen | |
| 7,050,536 B1 | 5/2006 | Fenkart | |
| 7,054,408 B2 | 5/2006 | Jiang | |
| 7,062,009 B2 | 6/2006 | Karimi | |
| 7,062,011 B1 | 6/2006 | Tybinkowski | |
| 7,062,074 B1 | 6/2006 | Beneke | |
| 7,064,334 B2 | 6/2006 | Hoffman | |
| 7,065,175 B2 | 6/2006 | Green | |
| 7,065,179 B2 | 6/2006 | Block | |
| 7,068,749 B2 | 6/2006 | Kollegal | |
| 7,068,750 B2 | 6/2006 | Toth | |
| 7,068,751 B2 | 6/2006 | Toth | |
| 7,072,434 B1 | 7/2006 | Tybinkowski | |
| 7,076,029 B2 | 7/2006 | Toth | |
| 7,078,699 B2 | 7/2006 | Seppi | |
| 7,081,628 B2 | 7/2006 | Granfors | |
| 7,084,404 B2 | 8/2006 | Hoffman | |
| 7,087,902 B2 | 8/2006 | Wang | |
| 7,088,799 B2 | 8/2006 | Hoffman | |
| 7,090,133 B2 | 8/2006 | Zhu | |
| 7,092,481 B2 | 8/2006 | Hoffman | |
| 7,092,485 B2 | 8/2006 | Kravis | |
| 7,103,137 B2 | 9/2006 | Seppi | |
| 7,110,488 B2 | 9/2006 | Katcha | |
| 7,112,797 B2 | 9/2006 | Hoge | |
| 7,116,749 B2 | 10/2006 | Besson | |
| 7,116,751 B2 | 10/2006 | Ellenbogen | |
| 7,119,553 B2 | 10/2006 | Yang | |
| 7,123,681 B2 | 10/2006 | Ellenbogen | |
| 7,127,027 B2 | 10/2006 | Hoffman | |
| 7,130,374 B1 | 10/2006 | Jacobs | |
| 7,133,491 B2 | 11/2006 | Bernardi | |
| 7,136,450 B2 | 11/2006 | Ying | |
| 7,136,451 B2 | 11/2006 | Naidu | |
| 7,139,367 B1 | 11/2006 | Le | |
| 7,139,406 B2 | 11/2006 | McClelland | |
| 7,142,629 B2 | 11/2006 | Edic | |
| 7,149,278 B2 | 12/2006 | Arenson | |
| 7,149,339 B2 | 12/2006 | Veneruso | |
| 7,155,812 B1 | 1/2007 | Peterson | |
| 7,158,611 B2 | 1/2007 | Heismann | |
| 7,164,747 B2 | 1/2007 | Ellenbogen | |
| 7,164,750 B2 | 1/2007 | Nabors | |
| 7,166,458 B2 | 1/2007 | Ballerstadt | |
| 7,166,844 B1 | 1/2007 | Gormley | |
| 7,167,539 B1 | 1/2007 | Hoffman | |
| 7,173,998 B2 | 2/2007 | Hoffman | |
| 7,177,387 B2 | 2/2007 | Yasunaga | |
| 7,177,391 B2 | 2/2007 | Chapin | |
| 7,190,757 B2 | 3/2007 | Ying | |
| 7,192,031 B2 | 3/2007 | Dunham | |
| 7,197,113 B1 | 3/2007 | Katcha | |
| 7,197,172 B1 | 3/2007 | Naidu | |
| 7,203,629 B2 | 4/2007 | Oezis | |
| 7,204,125 B2 * | 4/2007 | Fine | G01N 1/2202 422/83 |
| 7,206,379 B2 | 4/2007 | Lemaitre | |
| 7,212,113 B2 * | 5/2007 | Zanovitch | G08B 25/085 340/10.1 |
| 7,215,731 B1 | 5/2007 | Basu | |
| 7,215,738 B2 | 5/2007 | Muenchau | |
| 7,218,700 B2 | 5/2007 | Huber | |
| 7,218,704 B1 | 5/2007 | Adams | |
| 7,224,763 B2 | 5/2007 | Naidu | |
| 7,224,765 B2 | 5/2007 | Ellenbogen | |
| 7,224,766 B2 | 5/2007 | Jiang | |
| 7,224,769 B2 | 5/2007 | Turner | |
| 7,233,640 B2 | 6/2007 | Ikhlef | |
| 7,236,564 B2 | 6/2007 | Hopkins | |
| 7,238,945 B2 | 7/2007 | Hoffman | |
| 7,247,856 B2 | 7/2007 | Hoge | |
| 7,251,310 B2 | 7/2007 | Smith | |
| 7,257,189 B2 * | 8/2007 | Modica | G01V 5/0008 378/210 |
| 7,260,170 B2 | 8/2007 | Arenson | |
| 7,260,171 B1 | 8/2007 | Arenson | |
| 7,260,172 B2 | 8/2007 | Arenson | |
| 7,260,173 B2 | 8/2007 | Wakayama | |
| 7,260,174 B2 | 8/2007 | Hoffman | |
| 7,260,182 B2 | 8/2007 | Toth | |
| 7,263,160 B2 | 8/2007 | Schlomka | |
| 7,266,180 B1 | 9/2007 | Saunders | |
| 7,272,429 B2 | 9/2007 | Walker | |
| 7,274,767 B2 | 9/2007 | Clayton | |

(56) References Cited

U.S. PATENT DOCUMENTS

| | | | |
|---|---|---|---|
| 7,277,577 B2 | 10/2007 | Ying | |
| 7,279,120 B2 | 10/2007 | Cheng | |
| 7,280,631 B2 | 10/2007 | De | |
| 7,282,727 B2 | 10/2007 | Retsky | |
| 7,283,604 B2 | 10/2007 | De | |
| 7,283,609 B2 | 10/2007 | Possin | |
| 7,295,019 B2 | 11/2007 | Yang | |
| 7,295,651 B2 | 11/2007 | Delgado | |
| 7,298,812 B2 | 11/2007 | Tkaczyk | |
| 7,302,083 B2 | 11/2007 | Larson | |
| 7,308,073 B2 | 12/2007 | Tkaczyk | |
| 7,308,074 B2 | 12/2007 | Jiang | |
| 7,308,077 B2 | 12/2007 | Bijjani | |
| 7,317,195 B2 | 1/2008 | Eikman | |
| 7,317,390 B2 | 1/2008 | Huey | |
| 7,319,737 B2 | 1/2008 | Singh | |
| 7,322,745 B2* | 1/2008 | Agrawal | G01N 23/04 378/102 |
| 7,324,625 B2 | 1/2008 | Eilbert | |
| 7,327,853 B2 | 2/2008 | Ying | |
| 7,330,527 B2 | 2/2008 | Hoffman | |
| 7,330,535 B2 | 2/2008 | Arenson | |
| 7,333,587 B2 | 2/2008 | De | |
| 7,333,588 B2 | 2/2008 | Mistretta | |
| 7,333,589 B2 | 2/2008 | Ellenbogen | |
| 7,335,887 B1 | 2/2008 | Verbinski | |
| 7,336,769 B2 | 2/2008 | Arenson | |
| 7,349,525 B2 | 3/2008 | Morton | |
| 7,397,891 B2 | 7/2008 | Johnson | |
| 7,430,479 B1 | 9/2008 | Holslin | |
| 7,440,543 B2 | 10/2008 | Morton | |
| 7,492,855 B2 | 2/2009 | Hopkins | |
| 7,505,557 B2 | 3/2009 | Modica | |
| 7,512,215 B2 | 3/2009 | Morton | |
| 7,564,939 B2 | 7/2009 | Morton | |
| 7,580,505 B2 | 8/2009 | Kang | |
| 7,684,538 B2 | 3/2010 | Morton | |
| 7,734,066 B2* | 6/2010 | DeLia | B64F 1/368 378/57 |
| 7,734,102 B2* | 6/2010 | Bergeron | G01N 23/04 378/57 |
| 7,817,775 B2 | 10/2010 | Kang | |
| 7,903,783 B2 | 3/2011 | Modica | |
| 7,973,697 B2* | 7/2011 | Reilly | G01S 7/411 342/179 |
| 8,173,970 B2* | 5/2012 | Inbar | G01V 5/0075 250/390.07 |
| 8,243,167 B2 | 8/2012 | Liang | |
| 8,304,740 B1* | 11/2012 | Frank | G01V 5/0075 250/370.11 |
| 8,472,583 B2 | 6/2013 | Star-Lack | |
| 9,111,331 B2 | 8/2015 | Parikh | |
| 9,632,206 B2 | 4/2017 | Parikh | |
| 2001/0016684 A1 | 8/2001 | Shahidi | |
| 2001/0022346 A1 | 9/2001 | Katagami | |
| 2001/0033635 A1 | 10/2001 | Kuwabara | |
| 2002/0031202 A1 | 3/2002 | Callerame | |
| 2002/0038753 A1 | 4/2002 | Ursu | |
| 2002/0045152 A1 | 4/2002 | Viscardi | |
| 2002/0094064 A1 | 7/2002 | Zhou | |
| 2002/0172324 A1* | 11/2002 | Ellengogen | G01F 1/66 378/51 |
| 2002/0176531 A1 | 11/2002 | McClelland | |
| 2003/0021377 A1 | 1/2003 | Turner | |
| 2003/0023592 A1 | 1/2003 | Modica | |
| 2003/0031352 A1 | 2/2003 | Nelson | |
| 2003/0085163 A1* | 5/2003 | Chan | B64F 1/366 209/589 |
| 2003/0191557 A1* | 10/2003 | Takehara | G06Q 10/08 700/225 |
| 2004/0041724 A1* | 3/2004 | Levitan | F41H 13/00 342/22 |
| 2004/0073808 A1 | 4/2004 | Smith | |
| 2004/0080315 A1* | 4/2004 | Beevor | G01V 3/104 324/244 |
| 2004/0086078 A1 | 5/2004 | Adams | |
| 2004/0101098 A1* | 5/2004 | Bijjani | G01N 23/046 378/57 |
| 2004/0120454 A1 | 6/2004 | Ellenbogen | |
| 2004/0126015 A1* | 7/2004 | Hadell | B66C 13/46 382/181 |
| 2004/0140924 A1* | 7/2004 | Keller | G01N 21/3581 342/22 |
| 2004/0202154 A1* | 10/2004 | Aklepi | G06Q 10/08 370/352 |
| 2004/0212492 A1* | 10/2004 | Boesch | B64F 1/368 340/531 |
| 2004/0212499 A1 | 10/2004 | Bohinc | |
| 2004/0213378 A1 | 10/2004 | Zhou | |
| 2004/0213379 A1 | 10/2004 | Bittl | |
| 2004/0232054 A1* | 11/2004 | Brown | G01V 5/0008 209/552 |
| 2004/0251415 A1 | 12/2004 | Verbinski | |
| 2004/0252024 A1 | 12/2004 | Huey | |
| 2004/0252807 A1 | 12/2004 | Skatter | |
| 2004/0258198 A1* | 12/2004 | Carver | G01N 23/04 378/57 |
| 2004/0258305 A1 | 12/2004 | Burnham | |
| 2004/0263379 A1* | 12/2004 | Keller | G01N 21/3581 342/22 |
| 2005/0008119 A1 | 1/2005 | McClelland | |
| 2005/0024199 A1* | 2/2005 | Huey | B64F 1/366 340/521 |
| 2005/0031075 A1 | 2/2005 | Hopkins | |
| 2005/0031076 A1 | 2/2005 | McClelland | |
| 2005/0053189 A1 | 3/2005 | Gohno | |
| 2005/0064922 A1 | 3/2005 | Owens | |
| 2005/0105682 A1 | 5/2005 | Heumann | |
| 2005/0110672 A1* | 5/2005 | Cardiasmenos | G01N 21/3581 342/27 |
| 2005/0111610 A1 | 5/2005 | DeMan | |
| 2005/0117700 A1 | 6/2005 | Peschmann | |
| 2005/0156734 A1* | 7/2005 | Zerwekh | G01T 1/167 340/539.1 |
| 2005/0157844 A1* | 7/2005 | Bernardi | G01V 5/0016 378/57 |
| 2005/0157925 A1 | 7/2005 | Lorenz | |
| 2005/0169421 A1 | 8/2005 | Muenchau | |
| 2005/0198226 A1* | 9/2005 | DeLia | G06Q 10/02 709/220 |
| 2005/0226364 A1 | 10/2005 | Bernard | |
| 2005/0249416 A1 | 11/2005 | Leue | |
| 2005/0251397 A1* | 11/2005 | Zanovitch | G06Q 10/02 705/333 |
| 2005/0281390 A1 | 12/2005 | Johnson | |
| 2006/0018428 A1 | 1/2006 | Li | |
| 2006/0045323 A1* | 3/2006 | Ateya | G06K 9/2027 382/141 |
| 2006/0066469 A1* | 3/2006 | Foote | G01S 13/003 342/22 |
| 2006/0086794 A1* | 4/2006 | Knowles | G02B 26/10 235/454 |
| 2006/0113163 A1 | 6/2006 | Hu | |
| 2006/0115044 A1 | 6/2006 | Wu | |
| 2006/0115109 A1* | 6/2006 | Whitson | G01V 5/0083 382/100 |
| 2006/0138331 A1* | 6/2006 | Guillebaud | G01V 5/0075 250/359.1 |
| 2006/0220851 A1* | 10/2006 | Wisherd | G01S 5/06 340/568.1 |
| 2006/0257005 A1* | 11/2006 | Bergeron | G01N 23/04 382/103 |
| 2006/0273259 A1 | 12/2006 | Li | |
| 2006/0274916 A1* | 12/2006 | Chan | G06Q 10/06 382/100 |
| 2007/0003003 A1 | 1/2007 | Seppi | |
| 2007/0083414 A1 | 4/2007 | Krohn | |
| 2007/0096030 A1 | 5/2007 | Li | |
| 2007/0110215 A1 | 5/2007 | Hu | |
| 2007/0133740 A1 | 6/2007 | Kang | |

(56) References Cited

U.S. PATENT DOCUMENTS

| | | | |
|---|---|---|---|
| 2007/0165777 A1 | 7/2007 | Anwar | |
| 2007/0172024 A1 | 7/2007 | Morton | |
| 2007/0183568 A1 | 8/2007 | Kang | |
| 2007/0194909 A1* | 8/2007 | Garfield | G06K 9/00013 |
| | | | 340/521 |
| 2007/0195994 A1 | 8/2007 | McClelland | |
| 2007/0280416 A1* | 12/2007 | Bendahan | G01N 23/04 |
| | | | 378/57 |
| 2007/0280502 A1* | 12/2007 | Paresi | G01V 5/0083 |
| | | | 382/100 |
| 2008/0023631 A1* | 1/2008 | Majors | G01V 5/0075 |
| | | | 250/336.1 |
| 2008/0044801 A1 | 2/2008 | Modica | |
| 2008/0056432 A1 | 3/2008 | Pack | |
| 2008/0056435 A1 | 3/2008 | Basu | |
| 2008/0075230 A1 | 3/2008 | Oreper | |
| 2008/0111693 A1* | 5/2008 | Johnson | G01S 13/74 |
| | | | 340/572.1 |
| 2008/0143545 A1* | 6/2008 | King | B66C 13/16 |
| | | | 340/679 |
| 2008/0198967 A1 | 8/2008 | Connelly | |
| 2008/0260097 A1 | 10/2008 | Anwar | |
| 2009/0034790 A1 | 2/2009 | Song | |
| 2009/0161816 A1 | 6/2009 | DeMan | |
| 2009/0174554 A1 | 7/2009 | Bergeron | |
| 2009/0236531 A1 | 9/2009 | Frank | |
| 2009/0283690 A1 | 11/2009 | Bendahan | |
| 2009/0323894 A1 | 12/2009 | Hu | |
| 2010/0030370 A1* | 2/2010 | King | B65G 63/004 |
| | | | 700/214 |
| 2010/0161504 A1 | 6/2010 | Casey | |
| 2011/0060426 A1* | 3/2011 | Morton | G01V 5/0083 |
| | | | 700/73 |
| 2011/0172972 A1 | 7/2011 | Gudmundson | |
| 2011/0216881 A1 | 9/2011 | Modica | |
| 2012/0093367 A1 | 4/2012 | Gudmundson | |
| 2012/0105267 A1* | 5/2012 | DeLia | G01S 13/86 |
| | | | 342/22 |
| 2012/0300902 A1 | 11/2012 | Modica | |
| 2015/0325010 A1 | 11/2015 | Bedford | |

FOREIGN PATENT DOCUMENTS

| | | |
|---|---|---|
| DE | 3214910 A1 | 5/1983 |
| EP | 0176314 | 4/1986 |
| EP | 0432568 | 6/1991 |
| EP | 0531993 A1 | 3/1993 |
| EP | 0584871 A1 | 3/1994 |
| EP | 0924742 A2 | 6/1999 |
| EP | 0930046 A2 | 7/1999 |
| EP | 0963925 A2 | 12/1999 |
| EP | 1277439 A1 | 1/2003 |
| EP | 1374776 A1 | 1/2004 |
| EP | 2270547 | 1/2011 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2212903 A | 8/1989 |
| GB | 2337032 A | 11/1999 |
| GB | 2404431 | 2/2005 |
| GB | 2437777 A | 11/2007 |
| JP | 570175247 | 10/1982 |
| JP | 59016254 | 1/1984 |
| JP | 59075549 | 4/1984 |
| JP | 600015546 | 1/1985 |
| JP | 600021440 | 2/1985 |
| JP | 06038957 | 2/1994 |
| JP | H10211196 A | 8/1998 |
| JP | H11230918 A | 8/1999 |
| JP | 2001176408 | 6/2001 |
| JP | 2001233440 A | 8/2001 |
| JP | 2003126075 A | 5/2003 |
| JP | 2004000605 A | 1/2004 |
| JP | 2004079128 A | 3/2004 |
| JP | 2005013768 A | 1/2005 |
| JP | 2005257400 | 9/2005 |
| WO | 9528715 A2 | 10/1995 |
| WO | 9960387 A2 | 11/1999 |
| WO | 2000049428 | 8/2000 |
| WO | 03051201 A2 | 6/2003 |
| WO | 03105159 | 12/2003 |
| WO | 2004037088 | 5/2004 |
| WO | 2004111625 | 12/2004 |
| WO | 2005091227 | 9/2005 |
| WO | 2005084351 | 11/2006 |
| WO | 2006119603 A1 | 11/2006 |
| WO | 2006119605 | 11/2006 |
| WO | 2006119605 A1 | 11/2006 |
| WO | 2006135586 | 12/2006 |
| WO | 2007051092 | 5/2007 |
| WO | 2007055720 A2 | 5/2007 |
| WO | 2007103216 A2 | 9/2007 |
| WO | 2009106857 | 9/2009 |

OTHER PUBLICATIONS

Victor J. Orphan, Ernie Muenchau, Jerry Gormley, and Rex Richardson, "Advanced γ ray technology for scanning cargo containers," Applied Radiation and Isotopes, vol. 63, Issues 5-6, 2005, pp. 723-732.*

Viggo Butler and Robert W. Poole, Jr., Rethinking Checked-Baggage Screening, Reason Public Policy Institute, Policy Study 297, Jul. 2002.

McLay, Laura A., Jacobson, Sheldon H., and Kobza, John E., A multilevel passenger screening problem for aviation security, Naval Research Logistics (NRL), vol. 53, issue 3, pp. 183-197, 2006.

Sun Olapiriyakul and Sanchoy Das, Design and analysis of a two-stage security screening and inspection system, Journal of Air Transport Management, vol. 13, Issue 2, Mar. 2007, pp. 67-74.

Kelly Leone and Rongfang (Rachel) Liu, The key design parameters of checked baggage security screening systems in airports, Journal of Air Transport Management, vol. 11, Issue 2, Mar. 2005, pp. 69-78.

Rapiscan Security Products, Inc., Users Guide for Levels 1 and 2 Threat Image Protection (TIP) Users Manual, Jan. 12, 2001, document in general.

Rapiscan Security Products, Inc., Users Guide for Level 3 Threat Image Projection (TIP) System Manual, Aug. 4, 1999, document in general.

'Test and Evaluation Plan for Screener Proficiency Evaluation and Reporting System (SPEARS) Threat Image Projection' J.L.Fobes, Ph.D., et al. FAA, Dec. 1995.

'Revised Test and Evaluation Plan for Determining Screener Training Effectiveness' Brenda A. Klock, et al. FAA, Aug. 2000.

'Development and Validation of a Test of X-ray Screener Readiness' Eric C. Neiderman, Ph.D., et al. IEEE, 2000.

International Search Report for PCT/US2006/11492, dated Oct. 11, 2007, United Technologies Corporation.

International Search Report for PCT/US2007/005444, dated Oct. 29, 2007, Telesecurity Sciences, Inc.

International Search Report for PCT/GB2004/001747, dated Aug. 10, 2004, CXR Ltd.

International Search Report for PCT/GB2009/000575, dated Apr. 7, 2010, Rapiscan Security Products Inc.

Office Action dated Dec. 23, 2014 for U.S. Appl. No. 12/919,484.

Office Action dated Jul. 14, 2015 for U.S. Appl. No. 12/919,484.

Notice of Allowance dated Aug. 28, 2015 for U.S. Appl. No. 12/919,484.

International Search Report for PCT/GB09/00575, dated Apr. 7, 2010.

Summons to attend oral proceedings for EP097149108, Jun. 2, 2015.

First Examination Report for Indian Patent Application No. 6409/DELNP/2010, dated Apr. 26, 2017.

Pre-Examination Report for Brazilian Patent Application No. P1908881-4, dated Nov. 7, 2018.

(56) References Cited

OTHER PUBLICATIONS

ClearView Workstation, L3 Security & Detection Systems, Jun. 9, 2011.
International Search Report for PCT/US2017/017642, dated Jun. 29, 2017.
International Search Report for PCT/US2012/054110, dated Dec. 24, 2012.
First Examination Report for Australian Application No. 2012304490, dated Jul. 7, 2014.
Office Action for Canadian Patent Application No. 2849398, dated Sep. 21, 2018.
First Office Action for Chinese Patent Application No. CN201280054643.3, dated Aug. 27, 2015.
Third Office Action for Chinese Patent Application No. CN201280054643.3, dated Nov. 22, 2016.
Notification of Re-Examination for CN201280054643.3, dated Apr. 2018.
Notification of Re-Examination for CN201280054643.3, dated Oct. 30, 2018.
Horner et al., "Phase-Only Matched Filtering", Applied Optics, vol. 23, No. 6, Mar. 15, 1994, pp. 812-816.
Mahalanobis, et al. "Minimum Average Correlation Energy Filters", Applied Optics, vol. 26, No. 17, pp. 3633-3640, Sep. 1987.
Kumar et al. "Spatial frequency domain image processing for biometric recognition", Biometrics ICIP Conference 2002.
Caulfield, et al. "Improved Discrimination in Optical Character Recognition", Applied Optics, vol. 8, pp. 2354-2356, Nov. 1969.
Morin, et al. "Optical Character Recognition (OCR) in Uncontrolled Environments Using Optical Correlators", Proc. SPIE Int. Soc. Opt. Eng. 3715, 346; 1999.
Supplementary European Search Report for EP12830287, dated Feb. 27, 2015.
Examination Report for EP12830287.4, dated Jan. 18, 2016.
Examination Report for EP12830287.4, dated Oct. 31, 2016.
Examination Report for GB14049951, dated Jun. 26, 2015.
Examination Report for GB14049951, dated Dec. 4, 2015.
Examination Report for GB14049951, dated Jun. 27, 2016.
Examination Report for 2304/DELNP/2014, dated Apr. 12, 2018.
Office Action for JP2014529885, dated Jan. 28, 2016.
Notification of Preliminary Refusal for Korean Patent Application No. 10-2014-70008915, dated Oct. 22, 2018.

* cited by examiner

SCANNING SYSTEMS

CROSS REFERENCE

The present application is a national stage application of PCT/GB2009/000575, filed on Feb. 27, 2009, which further relies on Great Britain Patent Application Number 0803644.4, filed on Feb. 28, 2008, for priority. The applications are incorporated herein by reference in their entirety.

FIELD OF THE INVENTION

The present invention relates to scanning systems. It has particular application in scanning systems for cargo.

BACKGROUND

There is a requirement to be able to screen cargo items for the presence of illicit materials and devices for the protection of the public.

Currently, such inspection may be undertaken using X-ray based screening apparatus. In these systems, an X-ray image of the object under inspection is taken and an operator reviews this image to resolve, in their experience, whether the cargo is clear for onwards travel or whether the cargo requires a further level of inspection. However greater volumes of cargo traffic and greater desire and need for security scanning have lead to an increasing need to increase the throughput of scanning systems.

SUMMARY OF THE INVENTION

The present invention provides a cargo scanning system comprising a plurality of scanners each arranged to scan a respective object and generate a set of scan data, processing means arranged to process each set of scan data to determine whether it meets a predetermined threat condition, and data management means arranged to direct data that meets the threat condition to a workstation, or one of a plurality of workstations, for analysis.

The present application is directed toward cargo scanning systems having scanners, each arranged to scan a respective object and generate a set of scan data, processors arranged to process each set of scan data to determine whether it meets a predetermined threat condition, workstations, and a data management system arranged to direct data that meets the threat condition to one of the workstations for analysis.

The data management means may comprise a job dispatcher. The job dispatcher may be arranged to coordinate the tasks which are directed to each of the workstations. The data management means may further comprise a threat detection processor, which may be arranged to process image data to allocate the data to a threat category automatically, for example using one or more image processing algorithms. The data management means may also comprise a threat injector, which may be arranged to input test image data defining an image of a threat item. These different functions of the data management system can be provided as separate processors, or can be provided as different functions of a single processor.

The system may further comprise a cargo movement control means arranged to control movement of the objects through the scanners. Where the system is arranged to scan cargo carried on road-going vehicles the movement control means may include traffic lights and other signs and indicators for the driver of the vehicle. Where the system is arranged to scan rail cargo, the movement control means may include points on the railway. Where the system is arranged to scan cargo on a conveyor, the movement control means can include the conveyor.

The system may further comprise a holding bay and the movement control means may be arranged to hold one of the objects in the holding bay in response to the object meeting the threat condition. The movement control means may be arranged to cause the object to bypass the holding bay if it does not meet the threat condition.

According to some embodiments of the invention, a multi-level inspection process is provided which seeks to automate the scanning process to allow higher throughput and lower screening cost per cargo item.

The present invention further provides a method of scanning cargo comprising providing a plurality of scanners, scanning a respective object with each of the scanners to generate a respective set of scan data, processing each set of scan data to determine whether it meets a predetermined threat condition, and directing data that meets the threat condition to a workstation for analysis.

Preferred embodiments of the present invention will now be described by way of example only with reference to the accompanying drawings.

DETAILED DESCRIPTION OF THE INVENTION

Figure 1:
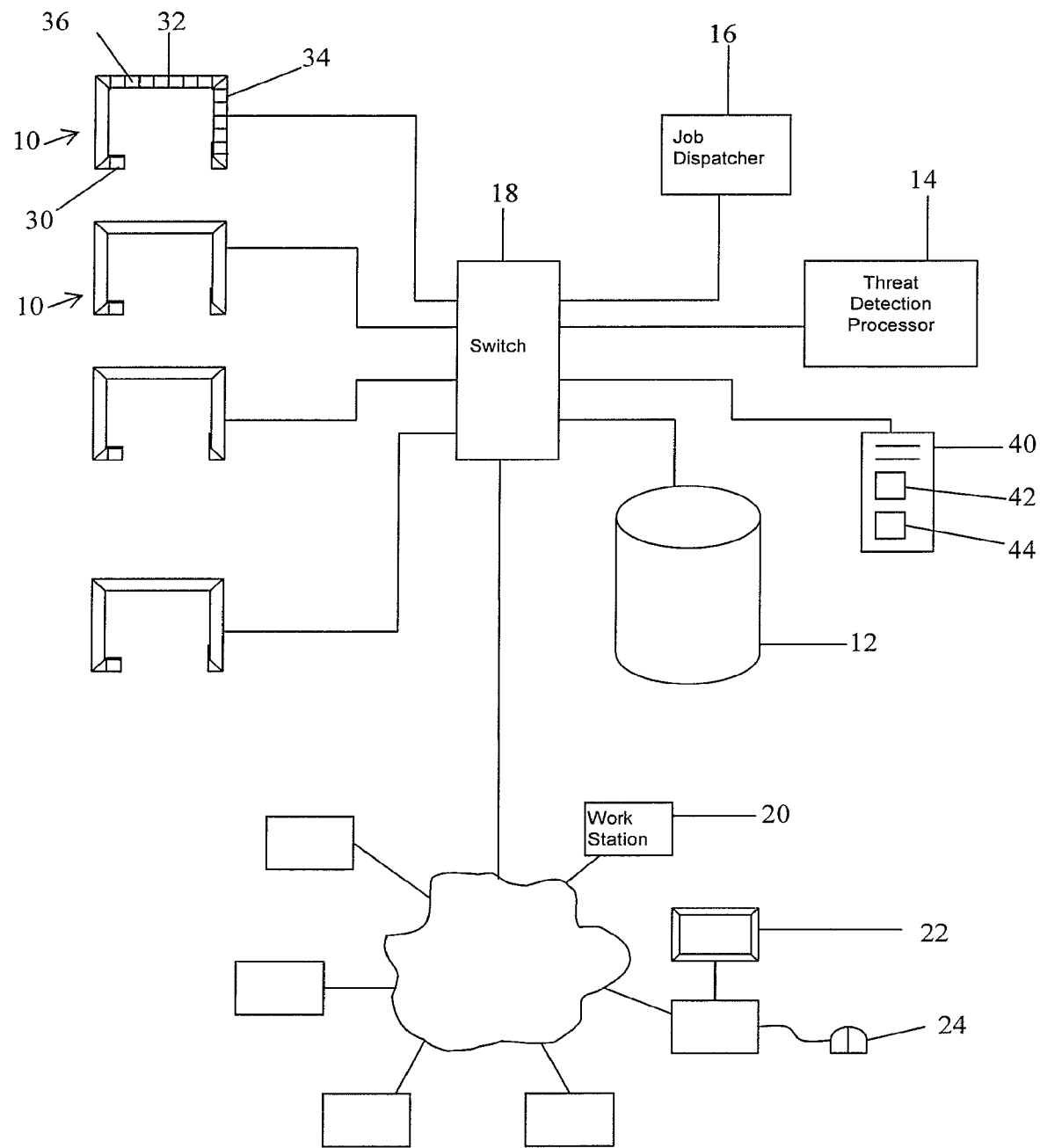
FIG. 1 is a schematic diagram of a scanning system according to an embodiment of the invention.

Referring to FIG. 1, a scanning system according to one embodiment of the invention comprises a number of scanners 10, which can be for example static, moving gantry or mobile scanners, each of which is arranged to scan a cargo container to generate image data. In this case the scanners 10 are arranged over a roadway 11 so that they can scan road-going cargo trucks. A storage array 12, threat detection processor 14 and job dispatcher 16, which generally includes a computer with a processor, are all connected to the scanners 10 and to each other by a data switch 18 or other suitable data transmission system. The data switch is also connected to a network of workstations 20. Each of the workstations 20 includes a display 22 arranged to display the image data in the form of an image for viewing by an operator, and a user input 24, in this case in the form of a mouse, which enables the operator to allocate one of a number of threat categories to each image.

The scanners 10 are able to operate independently and at high throughput. A typical scanner comprises an X-ray generator 30, a set of X-ray detector arrays 32, 34 each comprising a number of individual detectors 36 each arranged to generate an output signal. The scanner may be a drive-through scanner, or it may include means, such as a movable gantry, to scan the cargo item through an X-ray beam which fires from the X-ray generator 30 through the cargo item and onto the set of X-ray detectors 36. A two-dimensional image data set is formed by the scanner from the detector output signals. That data set contains information about the cargo item under inspection. In some embodiments more than one X-ray beam is used. In this case the beams may be used to generate two-dimensional image data sets, or three dimensional image data sets. In either case the image data from a series of scans is typically in a form that can be used to build up a three-dimensional image of the cargo item. The scanners 10 pass the image information through the data switch 18 which is able to route the information directly from the scanners 10 to the other nodes 12, 14, 16, 20. Typically, a scan will generate data in the form of Ethernet packets and the data switch 18 is therefore simply an Ethernet switch.

In the embodiment described here, data from the scanners 10 is passed directly to the central storage array 12 and the job dispatcher node 16 which is therefore arranged to receive from the generating scanner 10 the new cargo image data.

The job dispatcher 16 is then arranged, on receipt of any new image data set, to allocate time on the threat detection processor 14 for automated analysis of the new image data. Advantageously, the image data produced by the scanner 10 will have multi-energy attributes such that a detailed materials discrimination algorithm can be executed first by the threat detection processor 14, followed by an automated detection algorithm. Once the threat detection processor has analysed the image data produced by the scanner 10, it is arranged to notify the job dispatcher 16 of its conclusions.

If a threat item (e.g. a material or device) has been detected by the threat detection processor 14, the job dispatcher 16 is arranged to allocate an operator to review the image data produced by the scanner to resolve the severity of the threat item(s) that were detected by the threat detection processor 14, and to transmit the image data to one of the workstations 20, or simply make the data available for retrieval and analysis by the operator. The operator will utilise one of the networked operator workstations 20 that has the capability to manipulate the image data for optimal display.

Once the operator has made their decision, and input it as an operator decision input to the workstation using the input device 24, the result (either that the cargo is in fact clear for onwards travel or that it does indeed contain threat materials or devices) is forwarded to the job dispatcher 16 by the operator workstation. This can be done by sending the image data back with the decision attached to it in the form of a threat categorization, or by sending the decision, again for example as a threat categorization, with an identifier which uniquely identifies the image data set. The job dispatcher 16 is then arranged to notify the scanner 10 of the result.

In the event that a cargo item is flagged or categorized by the operator at the workstation 20 as containing a threat material or device, the facility manager is also notified, and a traffic management system controlled as described in more detail below to direct the cargo items appropriately, such that the threat cargo item can be quarantined until such time as an operative is available for manual search of the cargo item.

Typically, the threat detection processor 14 can be optimised to deliver a low false alarm rate to minimise the congestion and process delays that are caused when a threat cargo item is detected. The corollary of this is that the true detection rate will also be low. In this situation, very few operators are required in order to inspect image data from large numbers of scanning devices. This ensures a low screening cost per cargo item.

In this low false alarm rate scenario, it is reasonable to send a fraction of all the scanned images to the network of operators using random scheduling of cargo items which were cleared by the threat detection processor 14. This ensures that good inspection coverage of all the cargo items that are passing through the facility is achieved.

In a further mode of operation of the system, the balance between false alarm rate and detection probability is adjusted such that a higher detection rate is achieved but with a consequent increase in false alarm rate. In this scenario, more operators will be required in order to confirm or reject the cargo items following automated threat detection processing. At this higher false alarm rate level, it is unlikely that additional random inspection of automatically cleared containers will be required. The use of more operators pushes up the cost of screening containers but this comes at the benefit of an enhanced detection probability.

The threat detection processor 14 can be set to any particular sensitivity to suit the environment in which the system is to be used. However in this embodiment the sensitivity of the threat detection processor 14 is adjustable so that the operation of the system can be adjusted to suit the prevailing conditions. This means that where the threat detection processor is arranged to allocate each item to one of a number of threat categories, corresponding to different levels of threat, the category to which any particular images will be allocated can be adjusted so as to adjust the proportion of items that will be allocated to each of the categories. The threat detection processor can be arranged to adjust this allocation on the basis of one or more inputs, for example inputs indicative of an overall threat level, the volume of traffic which needs to be scanned, or the number of operators available to review the images. In a modification to this arrangement, the threat detection processor 14 can be arranged to allocate the items in the same way at all times, and the job dispatcher 16 can be made adjustable so that it allocates jobs to the workstations, and controls the flow of traffic in a way which is variable and adjustable in response to the same variables.

In a further embodiment of this invention, a further network node is added in the form of a threat injector 40. The threat injector node 40 comprises a computer 42 having a processor 44 and memory 46, with a library, stored in the memory 46, of images of threat items that have been collected under controlled conditions using scanners identical to those 10 in use in the installation. Using a scheduling algorithm that is controlled by the job dispatcher 16, image data that has been cleared by the threat detection processor 14 is passed to the threat injector 40. The threat injector 40 superimposes a threat object image from its library of stored images into the true cargo image in order to create a hybrid image that now contains a known threat in an otherwise clear image.

This hybrid image is then dispatched by the job dispatcher 16 to one of the workstations 20 for an operator review. The operator will be expected to find and mark the threat object. When the operator threat categorization decision is input at the workstation 20 and returned to the job dispatcher 16, the job dispatcher will send a notification to the workstation 20 to notify the operator that a known threat had been inserted into the image and will confirm whether the operator located the threat correctly. This information is then stored in a database of records, as part of one of the records which is relevant to the particular operator, in order to build up a picture of the individual operator's performance standard.

In a practical realisation of this invention, each workstation 20 can be arranged to display to an operator approximately 10% hybrid threat images, and 90% pure scanned images, in order to keep them occupied and well trained. The nature and complexity of the threat images that are injected are arranged to be variable and dependent on the identity of the operator, so that the testing can be balanced against the performance ability of the observer. This allows targeted training programmes to be established by the facility managers to ensure optimal human operation of the screening system.

In a modification to this system, instead of a hybrid image being generated as described above, a test image representing a threat object is simply selected from a library of test images and sent to one of the work stations 20, and the response of the operator monitored to see whether their categorization of the image is correct.

The job dispatcher 16 can be arranged to allocate jobs to individual workstations or workstation operators on the basis simply of the current workload of each operator, which the job dispatcher can determine from the tasks it has already allocated, and results it is waiting for from each operator, and the threat category to which the threat detection processor has allocated the item. However where the system has a record or profile associated with each operator, the allocation of tasks to operators can also be made on the basis of the profile. For example in some case the threat detection processor may allocate items to different categories not just on the basis of a level of threat that it associates with the item, but also on the basis of the type of threat, for example the type of threat object that has been detected or the category of threat material that has been detected. Where the operator profile includes types of threat that each operator is able to analyse, or a degree of proficiency of each operator at analysing each type of threat, the job dispatcher can allocate each task to an operator at least on the basis of this information to match each task to an operator suitable to perform it.

Each operator workstation 20 has the facility to annotate the displayed image, in response to inputs from the user input 24, in order to mark up an image to indicate the presence and type of threat objects and materials that have been detected in the cargo item.

Figure 2:
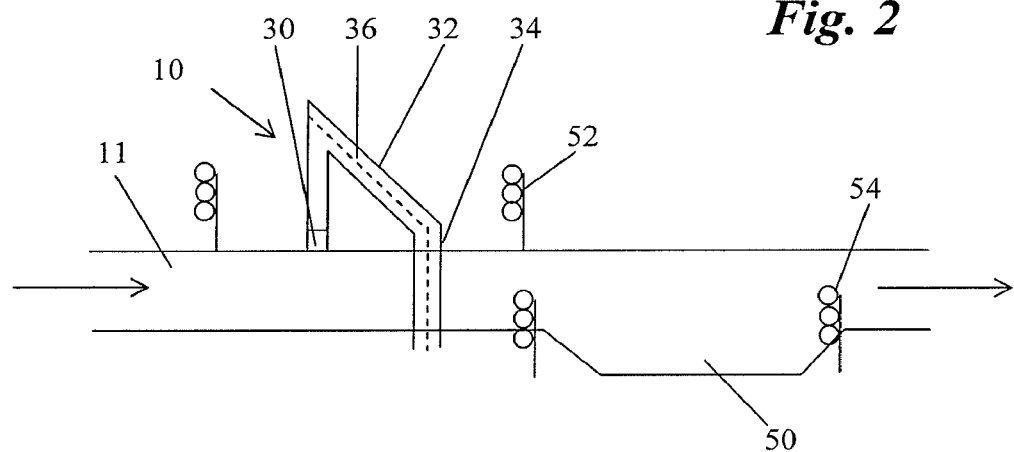
FIG. 2 is a schematic view of part of the scanning system of FIG. 1.

In a further modification to this embodiment of this invention, to facilitate the smooth operation of each scanning device 10, the job dispatcher 16 is able to cause the scanning system to route the passage of cargo items at its exit depending on the results of the automated detection processor and of any subsequent human inspection of the image data. For example, as shown in FIG. 2, each of the scanners 10 can have a holding bay 50 which a vehicle can enter after passing through the scanner, with a traffic control system, such as traffic lights 52, arranged to direct vehicles that have passed through the scanner 10 into the holding bay, or past the holding bay 50. If the automated threat detection processor 14 detected the presence of a threat item or material, of the traffic lights 52 adjacent to the scanner 10 will be controlled by the job dispatcher 16 to direct the load to the holding bay 50 until such time as the operator has input their response. When the operator response has been received by the job dispatcher 14 it is arranged to control further traffic controls, such as a further set of traffic lights 54, to indicate that the cargo is free to leave the scanning site, or that it needs to move on to another area for example for manual searching.

To maximise throughput of the installation, the automated threat detection processor 14 is arranged to generate a decision relating to a cargo item in a time period which is short compared to the overall scanning time for the cargo item. The job dispatcher 16 is arranged to be capable of allowing a scanner 10 to continue scanning new cargo items even if a cargo item is located in the associated holding bay 50 awaiting an operator decision.

The embodiments of FIGS. 1 and 2 are arranged to scan and control cargo carried on road vehicles, and the traffic management systems therefore rely on traffic lights and other suitable indicators or signs to direct the driver of the vehicle where to drive. However in another embodiment the system is arranged to scan cargo transported by rail. In this case the traffic management systems comprise traffic lights and also points on the rail tracks, for example at the exits 62 from the scanners in FIG. 3, that can be switched to determine the route which the cargo takes.

The job dispatcher 16 is also arranged to control queuing of multiple suspect cargo items in the holding bay in order to maximise throughput of the screening installation.

Figure 3:
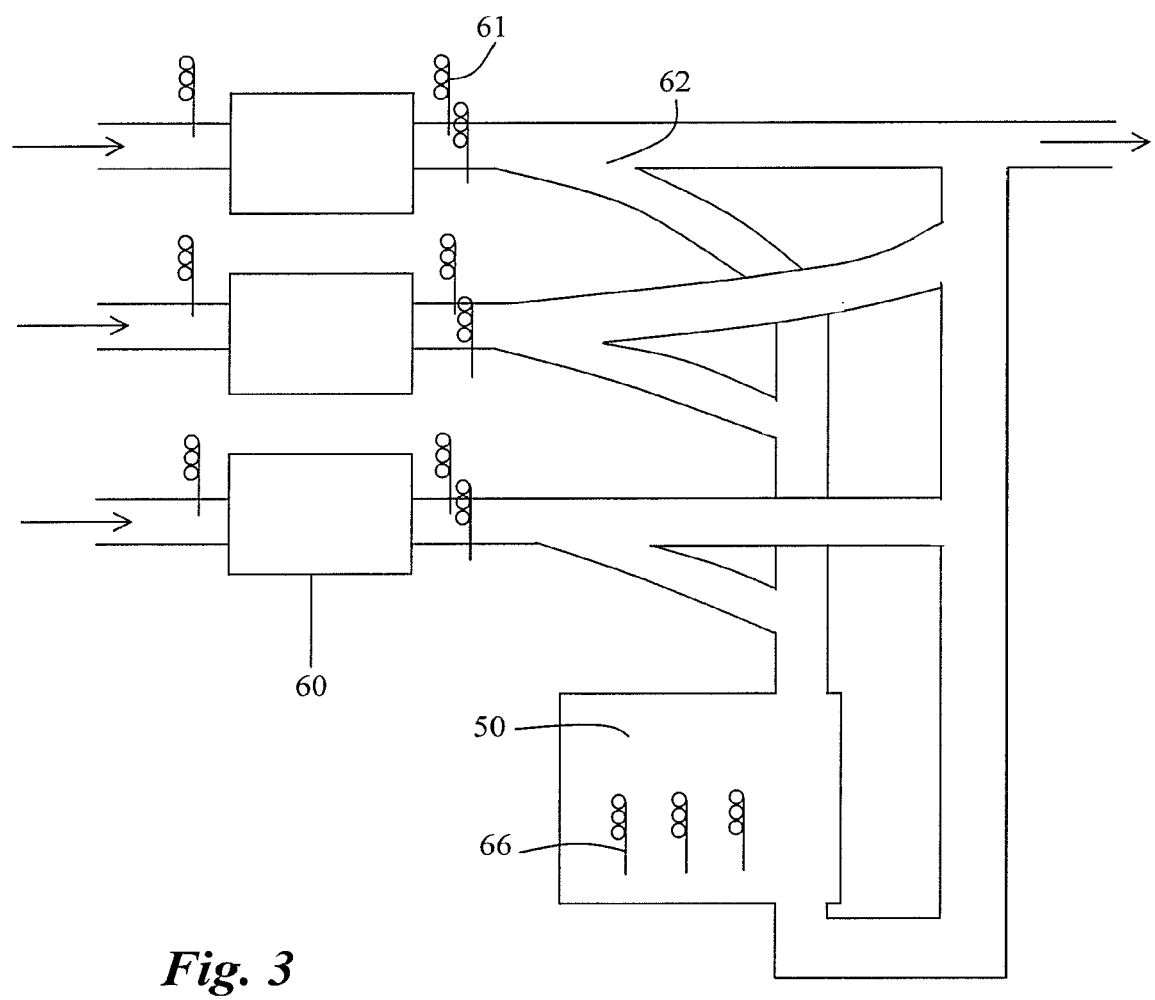
FIG. 3 is a schematic plan view of a scanning system according to a further embodiment of the invention.

Referring to FIG. 3, in a further embodiment, a security installation is similar to that of FIG. 2 but comprises a number of scanners 60, each with an associated traffic control system 61, and arranged to scan cargo items in parallel. The exits 62 from all of the scanners 60 lead to a shared quarantine area 64 that serves all of the scanning systems 60. The traffic control systems 61 which comprise traffic lights or equivalent traffic management systems, are arranged to direct traffic either straight through scanners 60 to the exit of the scanning installation or, in the event of a threat being detected, to direct the load to the quarantine area 64 where further traffic management systems 66 are provided and arranged to route cargo loads to the exit of the installation following manual search as required.

Figure 4:
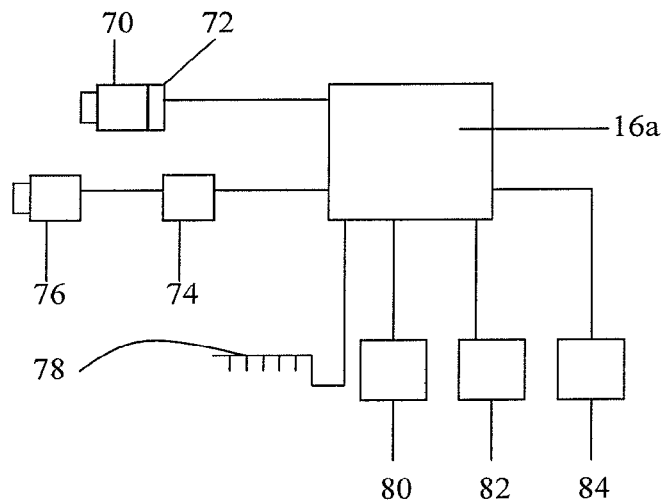
FIG. 4 is a schematic diagram of a threat detection system forming part of a scanning system according to a further embodiment of the invention.

Referring to FIG. 4, in further embodiments of the invention, which can be otherwise similar to those of FIGS. 1 to 3, the job dispatcher 16a is similar to that of FIG. 1, but is also arranged to receive, use and manage one or more different forms of information in addition to X-ray image data. This could typically include video images of the cargo load, which the job dispatcher 16a is arranged to receive from one or more video cameras 70. It can also include optical character recognition data related to container numbering, which can either be obtained by an image processor 72 arranged to process images from the video cameras, or a separate processor 74 arranged to receive and process images from an imaging device 76 specifically arranged to image a part of the container that carries the numbering. The information can also include scanned images of manifest information that may be provided with the cargo item. It may include data from secondary sensors such as weighbridge data from a weighbridge 78 indicative of the weight of the container, data from chemical detectors or 'sniffers' 80 indicative of the presence of one or more chemical compounds in the container, passive gamma ray data from a gamma ray detector 82 or neutron sensing data from a neutron sensor 84. The secondary sensors are shown here is present at the scanner site and part of the installation, but any of them can equally be at a separate location, and arranged to store the data they provide on a data carrier so that it can be input to the job dispatcher, or to transmit the data to the job dispatcher with some form of identification of the container it relates to. Where this ancillary data is available, the job dispatcher 16a is typically arranged to pass the data to the automated threat detection processor which is arranged to use it as an input to the threat detection algorithm that it uses in order to assist it in making the best possible threat categorization decision.

Figure 5:
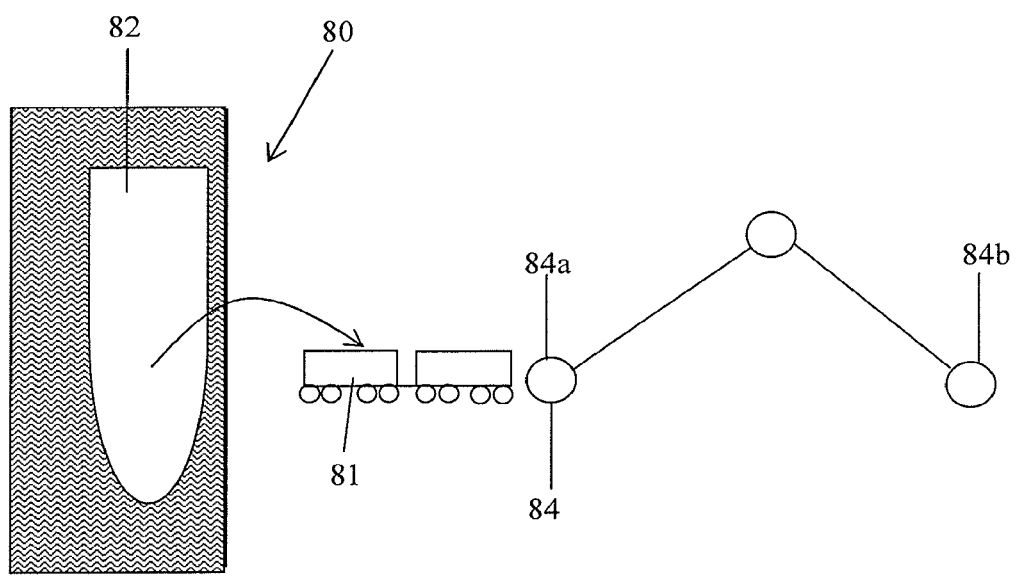
FIG. 5 is a schematic diagram of a cargo security system according to a further embodiment of the invention.

Referring to FIG. 5, in a further embodiment of the invention a cargo security system is similar to that of FIGS.

3 and 4, but the system is arranged to scan cargo carried by rail on a rail train 81. The parts of the system are distributed over larger distances so as to enable an efficient flow of cargo traffic. The system is arranged to scan and categorize cargo arriving at a port 80 on a vessel 82. The system includes a number of scanners, and all of the sources of secondary data described above with reference to FIG. 4, but these are distributed at a number of locations 84 along the rail route between the port 80 and a final quarantine or checking area. In particular the scanners 60 are at one location 84a close to the port 80 where they can be used to scan the cargo shortly after it has been loaded onto the rail vehicle 81, and the final checking area is provided at another location 84b further away from the port which may be at a destination of the cargo where it is removed from the rail vehicle 81 carrying it, and any individual cargo items or containers which are identified as a possible threat can be checked without delaying the progress of containers which are not identified as a threat. A traffic management system similar to that of FIG. 3 including rail points and traffic lights is used to control the route of each item of cargo, into or past the checking area 86, dependent on the analysis of the scan data and other secondary data by the threat detection processor. This arrangement means that the cargo items do not need to be delayed close to the port 80, and can be moving away from the port, and towards their final destination, while the threat detection analysis is being performed.

I claim:

1. A cargo scanning system, wherein the cargo is positioned inside a plurality of containers, comprising:
   a plurality of scanners each arranged to scan at least one of the plurality of containers, generate sets of scan data, and communicate the sets of scan data to a network;
   a central storage array in data communication with the network and configured to receive the sets of scan data from each of the plurality of scanners;
   one or more workstations in data communication with the network, wherein each of the one or more workstations is configured to receive a user input;
   an imaging device configured to capture images of characters associated with the at least one of the plurality of containers;
   an imaging processor configured to generate optical character recognition data indicative of the characters associated with the at least one of the plurality of containers;
   a job dispatcher in data communication with the network and configured to execute a process for automatically allocating the sets of scan data to at least one of the one or more workstations for analysis, to make the sets of scan data available to the one of the one or more workstations, to receive and direct data indicative of the characters associated with the at least one of the plurality of containers and manifest information related to the cargo and to generate a hybrid set of scan data by combining a threat object image from a library of threat object images with one of the sets of scan data;
   a cargo movement control means arranged to control movement of the at least one of the plurality of containers; and
   an area wherein the cargo movement control means is arranged to control movement of the at least one of the plurality of containers into or within the area if the user input allocates the at least one of the plurality of containers to one of a plurality of predetermined threat categories.

2. The system according to claim 1, wherein the job dispatcher is arranged to control a supply of data from the sets of scan data to a processing means, wherein the processing means is configured to process each of the sets of scan data to determine whether portions of the sets of scan data meets one of the plurality of predetermined threat categories.

3. The system according to claim 2 wherein the processing means is arranged to receive at least one set of secondary data associated with the at least one of the plurality of containers and to process the secondary data as well as the sets of scan data to determine whether a threat condition is met.

4. The system according to claim 3 wherein the secondary data comprises at least one of the following: weighbridge data, chemical detector data, gamma ray detector data or neutron sensor data.

5. The system according to claim 2 wherein the processing means is further configured to execute a process for automatically determining whether the at least one of the plurality of containers associated with each of the sets of scan data are cleared and to transfer a fraction of the sets of scan data associated with the at least one of the plurality of containers that are cleared to the one or more workstations.

6. The system according to claim 1 wherein the job dispatcher is arranged to transmit the sets of scan data to the one or more workstations.

7. The system according to claim 1 wherein the user input at each of the one or more workstations is configured to enable a user to provide an input allocating the sets of scan data to one of the plurality of predetermined threat categories.

8. The system according to claim 1 further comprising a holding bay wherein the cargo movement control means is arranged to hold the at least one of the plurality of containers in the holding bay in response to the at least one of the plurality of containers being allocated to one of the plurality of predetermined threat categories.

9. The system according to claim 8 wherein the cargo movement control means is arranged to cause the at least one of the plurality of containers to bypass the holding bay if the at least one of the plurality of containers does not meet a threat condition.

10. The system according to claim 1 wherein the cargo movement control means is arranged to control movement of the at least one of the plurality of containers so as to bypass the area if the user input does not allocate it to one of the plurality of the predetermined threat categories.

11. The system according to claim 1 wherein a data management means is arranged to generate a profile of an accuracy of the user's allocation of the sets of scan data to the one of the plurality of predetermined threat categories.

12. The system according to claim 1 wherein the threat object image is combined with the one of the sets of scan data by superimposing the threat object image onto an image corresponding to the one of the sets of scan data.

13. The system according to claim 1 wherein the one of the sets of scan data combined with the threat object image corresponds to an image of cargo without a threat.

14. The system according to claim 1 wherein the one or more workstations is further configured to receive a user input that identifies the threat object image in the hybrid set of scan data as being a threat.

15. The system according to claim 14 wherein the job dispatcher is configured to receive the user input identifying the threat object in the hybrid set of scan data as being a threat and send a notification to the one or more workstation that a known threat had been inserted into the one of the sets of scan data.

16. The system according to claim 14 wherein the job dispatcher is further configured to store in the central storage array a record of whether an operator of the one or more workstations correctly identified the threat object image in the hybrid set of scan data as being a threat.

17. The system according to claim 1 wherein a type of the threat object image combined with the one of the sets of scan data is dependent upon an identity of an operator of one of the one or more workstations.

\* \* \* \* \*